(12) United States Patent
Kwon et al.

(10) Patent No.: US 7,939,542 B2
(45) Date of Patent: May 10, 2011

(54) CINNAMALDEHYDE DERIVATIVES HAVING IMPROVED SOLUBILITY IN WATER, A METHOD FOR PREPARING THE SAME AND A PHARMACEUTICAL COMPOSITION COMPRISING THE SAME

(75) Inventors: Byoung Mog Kwon, Yuseong-gu (KR); Dong Cho Han, Yuseong-gu (KR); Hye Nan Kim, Dong-gu (KR); Young Min Han, Yuseong-gu (KR); Dae Seop Shin, Goesan-gun (KR); Yeong Rim Kang, Yeosu-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 77 days.

(21) Appl. No.: 12/200,548

(22) Filed: Aug. 28, 2008

(65) Prior Publication Data

US 2009/0325972 A1 Dec. 31, 2009

(30) Foreign Application Priority Data

Jun. 25, 2008 (KR) .................. 10-2008-0060096

(51) Int. Cl.
*A01N 43/40* (2006.01)
*A61K 31/435* (2006.01)
*C07D 213/00* (2006.01)

(52) U.S. Cl. ...................... 514/277; 546/339
(58) Field of Classification Search .................. 514/277; 546/339

See application file for complete search history.

(56) References Cited

U.S. PATENT DOCUMENTS 5,167,693 A * 12/1992 Drewes et al. ................ 504/196
6,949,682 B2 9/2005 Kwon

FOREIGN PATENT DOCUMENTS

KR 10-2006-0104554 A 10/2006

OTHER PUBLICATIONS

Byoung-Mog Kwon, et al., Synthesis and In Vitro Cytotoxicity of Cinnamaldehydes to Human Solid Tumor Cells, Arch. Pharm. Res. vol. 21, No. 2, 147-152 (1998).*
Han, et al., 2'-Benzolyoxycinnamaldehyde Induces Apoptosis in Human Carcinoma via Reactive Oxygen Species, J. Biol. Chem., vol. 279, No. 8, 6911-6920 (2004).*
Shin, et al., Synthesis and Biological Evaluation of Cinnamyl Compounds as Potent Antitumor Agents, Bioorganic & Medicinal Chemistry Letters vol. 17, 5423-5427 (2007).*
Shin, et al., Synthesis and Biological Evaluation of Dimeric Cinnamaldehydes as Potent Antitumor Agents Bioorganic & Medicinal Chemistry Letters 17, 2498-2506 (2006).*
Dong Cho Han et al. 2'-Benzoyloxycinnamaldehyde Induces Apoptosis in Human Carcinoma via Reactive Oxygen Species, The Journal of Biological Chemistry, vol. 279, No. 8, Issue of Feb. 20, 2004, pp. 6911-6920.
Dae-Seop Shin et al., Synthesis and Biological Evaluation of Dimeric Cinnamaldehydes as Potent Antitumor Agents, Bioorganic & Medicinal Chemistry, vol. 14 (2006), pp. 2498-2506.
Dae-Seop Shin et al., Synthesis and Biological Evaluation of Cinnamyl Compounds as Potent Antitumor Agents, Bioorganic & Medicinal Chemistry Letters, vol. 17 (2007), pp. 5423-5427.
Peter L. Toogood, Progress Toward The Development of Agents to Modulate the Cell Cycle, Current Opinion in Chemical Biology, 2002, 6, pp. 472-478.
Marcus Malumbres et al., To Cycle or Not to Cycle: A Critical Decision in Cancer, Nature Review Cancer 1, Dec. 2001, vol. 1, pp. 222-231.
Korean Priority Application 10-2008-0060096 filed Jun. 25, 2008, Notice of Allowance issued May 31, 2010 (in Korean).
Kwon, Byoung-Mog, et al., "Synthesis and in Vitro Cytotoxicity of Cinnamaldehydes to Human Solid Tumor Cells"; Arch. Pharm. Res.; vol. 21, No. 2; 1998; pp. 147-152.

* cited by examiner

*Primary Examiner* — James O Wilson
*Assistant Examiner* — Erich A Leeser
(74) *Attorney, Agent, or Firm* — Arent Fox LLP

(57) ABSTRACT

Disclosed herein are a novel cinnamaldehyde compound represented by Chemical Formula 1 or pharmaceutically acceptable salts thereof. The cinnamaldehyde compound has improved solubility in water and has inhibitory effects on the growth of cancer cells because it induces cell cycle arrest and cell death. Also disclosed are a method of preparing the cinnamaldehyde compound and an anticancer composition including the compound of Chemical Formula 1.

[Chemical Formula 1]

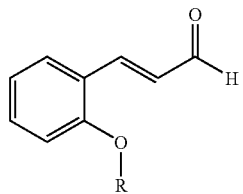

9 Claims, 3 Drawing Sheets

CINNAMALDEHYDE DERIVATIVES HAVING IMPROVED SOLUBILITY IN WATER, A METHOD FOR PREPARING THE SAME AND A PHARMACEUTICAL COMPOSITION COMPRISING THE SAME

BACKGROUND OF THE INVENTION

1. Field of the Invention

The present invention relates to novel cinnamaldehyde derivatives. More particularly, the present invention relates to novel cinnamaldehyde derivatives or pharmaceutically acceptable salts thereof having improved solubility in water, a method of preparing the same, and an anticancer composition comprising the same.

2. Description of the Related Art

Division, proliferation and differentiation of cells constituting the body are vital processes for the maintenance of life phenomena. Cellular proliferation and growth necessary for maintaining the normal functions of cells are regulated through sophisticated intracellular signal transduction systems. Once cells recognize a signal from the outside, a cascade of intracellular signaling events is activated to transfer the external signal to the cellular clock within the nucleus through several proteins (PLC, PKC, Shc, Grb2, Raf, MAPK, MEK, etc.) and molecular mediators (GTP, cAMP, etc.). When an abnormality occurs in any one of the signaling events, the events are balanced by their own regulatory mechanisms, but the abnormality often leads to disease. In particular, the cell cycle, during which events happen in the nucleus of cells, is a process essential for controlling the maintenance of cells.

Like a clock, which is composed of three counters for seconds, minutes and hours, the cell cycle consists of four different phases: G1 (Gap1), S (DNA synthesis), G2 (Gap2) and M (mitosis) phases. In addition to the phases, when cells are present at a high density or exposed to low concentrations of growth factors for a long period, they enter the resting phase (G0), in which cells stop dividing. These events, occurring in the nucleus, are referred to as the cell cycle.

In a clock, a clock pendulum is driven to oscillate using electric or physical force to rotate second, minute and hour counters in clockwise directions, thereby precisely displaying the time. For this, a predetermined force should be applied to the pendulum, and many other parts are thus needed. Likewise, the cell cycle process is controlled by a complex network of surveillance mechanisms, called checkpoints, which allow for the cellular clock to proceed in a defined sequence of G1-S-G2-M phases. There are two main checkpoints: one at the G1/S transition and another at G2/M. Cell cycle checkpoints check whether requirements for cells to progress to the next phase of the cycle are satisfied. When all requirements are satisfied, cells enter the S phase or M phase. Loss of checkpoint regulatory mechanisms increases genomic instability, resulting in uncontrolled cell growth and sometimes eventually tumorigenesis, such as cancer.

If signaling from outside the nucleus and nutritional conditions are favorable, cells become larger in size in the G1 phase and then enter the cell cycle. The cell cycle starts at the G1 checkpoint, which is called START in yeast and the restriction point in mammals. After passing this stage, if there is no specific disturbance, cells progress automatically through the four-phase cell cycle to duplicate their genomes and to divide. In detail, in mammalian cells, the G1 phase, having a checkpoint, is the preparation period for creating new cells. At this stage, if growth factors and sufficient nutrients are not supplied to cells, cells stops progressing through the cell cycle and enter the quiescent phase, G0. In contrast, if sufficient nutrients are supplied and various growth factors are provided, cells enter the S phase. During the S phase, cells duplicate their DNA to have two copies of the chromosome, and synthesize several cytoplasmic factors needed to split themselves into two daughter cells. After the S phase is completed, cells enter the G2 phase, which is called the second checkpoint. During the G2 phase, DNA replication is regulated and completed, and cells prepare to undergo mitosis (the M phase). A variety of factors required for cell organization are produced during this phase. After factors required for division into two daughter cells are sufficiently synthesized, cells progress to the M phase, in which substantial cell division occurs. The M phase is the shortest and most dramatic stage among the four phases of the cell cycle. That is because the two pairs of chromosomes are segregated toward opposite poles of cells to thus divide the cells into two daughter cells. These events are a process that all cells undergo in order to grow and divide themselves into two cells, and are thus very important for maintaining the cell's life. Therefore, the studies on the cell cycle and the development of modulators for the cell cycle are essential for the understanding of cell growth mechanisms and the development of preventive and therapeutic agents for cancer caused by abnormalities in the cell cycle (Marcos Malumbres and Mariano Barbacid, Nature Review Cancer 2001, 1, 222-231).

As noted above, mammalian cell growth can be regulated by controlling the first checkpoint in the G1 phase or the second checkpoint in the G2/M phase. Aberrant progression of the two checkpoints is associated with cellular aging or the development of diseases, such as cancer. Cyclins D1, D2 and D3 play important roles at the cell cycle checkpoints. The D-type cyclins are associated with cyclin-dependant kinase (CDK) 2, 4 or 6 to regulate the activity of the enzyme, and protein phosphatases, such as CDC25, which dephosphorylate phosphorylated proteins, are very important regulators in the entire cell cycle. Based on the previous findings, various cell cycle regulators have been developed as therapeutic agents for stubborn diseases, such as tumors (Peter L Toogood, Current Opinion in Chemical Biology 2002, 6, 472-478).

Cinnamaldehyde derivatives have been reported to have anticancer activity, but have very low solubility in water, which limits their application as anticancer agents. For example, benzoyloxy cinnamaldehyde exhibits good anticancer activity in cells as well as when administered intraperitoneally to animals. However, due to its very low water solubility, the compound cannot be applied to intravenous administration and has greatly decreased anticancer activity when administered orally (Han, D. C., et al., *J. Biol. Chem.* 2004, 279, 6911-6920). Although various cinnamaldehyde derivatives have been developed, they do not have good anticancer activity when applied to animals due to their low water solubility (Shin D. S. et al., Bioorganic & Medicinal Chemistry Letters 17 (2007) 5423.5427; Bioorganic & Medicinal Chemistry 14 (2006) 2498.2506; Byoung-Mog Kwon, et al., U.S. Pat. No. 6,949,682, 2005; Korean Pat. No. 10-0668171, filed by Byoung-Mog Kwon, et al.).

In this regard, the present inventors have developed novel cinnamaldehyde derivatives or pharmaceutically acceptable salts thereof, which arrest the cell cycle of cancer cells in G2/M phase to inhibit the abnormal growth of the cells and thus have good anticancer activity, thereby leading to the present invention.

SUMMARY OF THE INVENTION

It is therefore an object of the present invention to provide a novel cinnamaldehyde derivative or a pharmaceutically acceptable salt thereof having improved solubility in water.

It is another object of the present invention to provide a method of preparing the novel cinnamaldehyde derivative or pharmaceutically acceptable salt thereof.

It is a further object of the present invention to provide an anticancer composition comprising the novel cinnamaldehyde derivative or pharmaceutically acceptable salt thereof as an effective ingredient.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
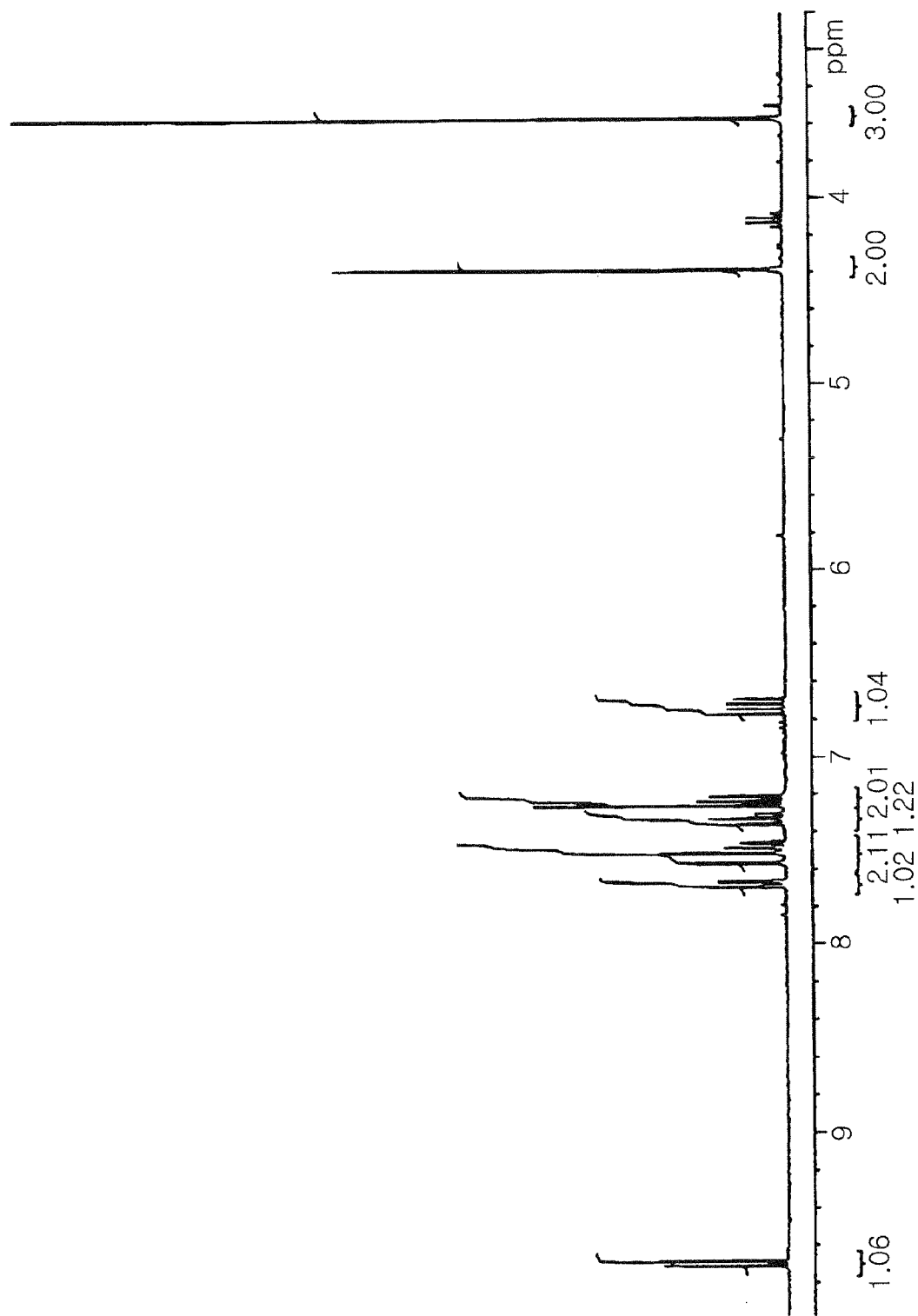
FIG. 1 is a proton NMR spectrum of a compound represented by Chemical Formula 2.

In one aspect, the present invention provides a cinnamaldehyde compound represented by Chemical Formula 1, below, or a pharmaceutically acceptable salt thereof.

[Chemical Formula 1]

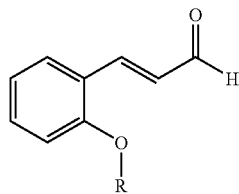

Wherein, R is selected from ($C_1$-$C_3$) alkoxy ($C_1$-$C_4$) alkylcarbonyl, 6-membered heterocyclic carbonyl unsubstituted or substituted with one or more ($C_1$-$C_4$) alkyl and having one or two heteroatoms selected from oxygen and nitrogen, ($C_4$-$C_{10}$) heteroaryl having one or more nitrogen heteroatoms, and sulfonyl substituted with ($C_6$-$C_{10}$) aryl.

Preferably, in Chemical Formula 1, R is selected from methoxyacetyl, piperazinecarbonyl unsubstituted or substituted with one or more ($C_1$-$C_2$) alkyl, picolyl, and benzenesulfonyl.

In a further preferred aspect, the present invention provides a compound selected from the group consisting of Chemical Formulas 2 to 7, below, or a pharmaceutically acceptable salt thereof.

[Chemical Formula 2]

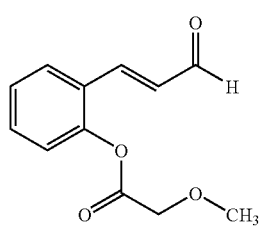

[Chemical Formula 3]

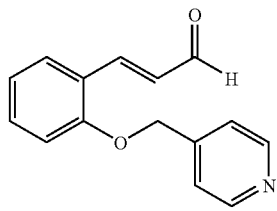

[Chemical Formula 4]

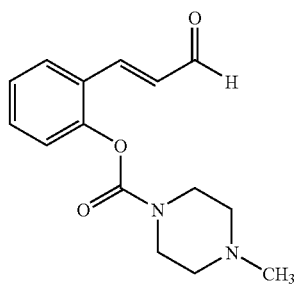

[Chemical Formula 5]

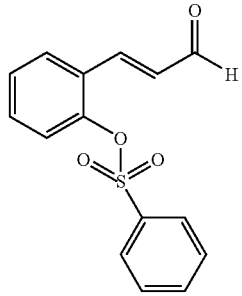

[Chemical Formula 6]

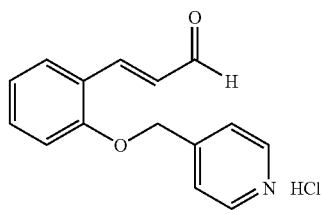

[Chemical Formula 7]

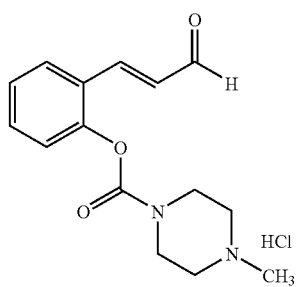

As used herein, the term "alkoxy" refers to a lower alkoxy group having 1 to 3 carbon atoms, and includes, for example, methoxy, ethoxy and propoxy.

As used herein, the term "alkyl" refers to a straight or branched radical having 1 to 4 carbon atoms, and includes, for example, methyl, ethyl, n-propyl, iso-propyl, n-butyl, iso-butyl and tertiary butyl.

As used herein, the term "heterocyclic" refers to a 6-membered ring having one or two heteroatoms selected from oxygen and nitrogen heteroatoms, but is meant not to include an aromatic ring. Examples of heterocyclic rings include piperazine and morpholine. Piperazine is particularly preferred.

As used herein, the term "heteroaryl" refers to a mono- or poly-cyclic aromatic ring having 4 to 10 carbon atoms and one or more nitrogen heteroatoms, and includes, for example, picolyl, pyridine, pyrimidine, pyrazine and pyridazine. Picolyl is particularly preferred.

As used herein, the term "aryl" refers to a mono- or polycyclic aromatic ring having 6 to 10 carbon atoms, and includes, for example, phenyl and naphthyl. Phenyl is particularly preferred.

As used herein, the term "leaving group" refers to a halogen atom (e.g., chlorine, bromine, iodine etc.), toluenesulfonyloxy, methanesulfonyloxy, etc.

The compounds of Chemical Formula 1 according to the present invention may also be prepared in the form of pharmaceutically acceptable salts and solvates thereof using common methods in the art.

The salt useful in the present invention is an acid addition salt formed with a pharmaceutically acceptable free acid. An acid addition salt may be prepared using a common method, for example, by dissolving a compound in an excess amount of aqueous acid solution and precipitating the salt formed using a water-miscible organic solvent, such as methanol, ethanol, acetone or acetonitrile. Alternatively, an acid addition salt may be formed by heating an equimolar amount of a compound and an acid in water or alcohol (e.g., glycol monomethyl ether), and subsequently evaporating the mixture until dry or filtering the precipitated salt under suction.

The free acid may be an inorganic acid or an organic acid. Examples of the inorganic acids include, but are not limited to, hydrochloric acid, phosphoric acid, sulfuric acid, nitric acid and stannic acid. Examples of the organic acids include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering the undissolved salt, and then evaporating the filtrate until dry. As the metal salts, sodium, potassium or calcium salts are pharmaceutically suitable, but the present invention is not limited thereto. Also, the corresponding silver salts may be obtained by reacting an alkali metal or alkaline earth metal salt with a proper silver salt (e.g., silver nitrate).

Pharmaceutically acceptable salts of the compound of Chemical Formula 1, unless otherwise indicated herein, include salts of acidic or basic groups, which may be present in the compound of Chemical Formula 1. For example, the pharmaceutically acceptable salts include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

In another aspect, the present invention provides a method of preparing a cinnamaldehyde compound represented by Chemical Formula 1 or a pharmaceutically acceptable salt thereof, comprising the step of 1) reacting hydroxycinnamaldehyde, represented by Chemical Formula 8, below, with a compound represented by Chemical Formula 9 to yield the compound of Chemical Formula 1.

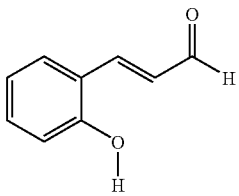

[Chemical Formula 8]

R—Z                 [Chemical Formula 9]

wherein R is selected from $(C_1-C_3)$ alkoxy $(C_1-C_4)$ alkylcarbonyl, 6-membered heterocyclic carbonyl unsubstituted or substituted with one or more $(C_1-C_4)$ alkyl groups and having one or two heteroatoms selected from oxygen and nitrogen, $(C_4-C_{10})$ heteroaryl having one or more nitrogen heteroatoms, and sulfonyl substituted with $(C_6-C_{10})$ aryl; and Z is a leaving group.

Preferably, in Chemical Formula 9, R is selected from methoxyacetyl, piperazinecarbonyl unsubstituted or substituted with one or more $(C_1-C_2)$ alkyl, picolyl, and benzenesulfonyl; and Z is chlorine (Cl) or Bromine (Br).

An exemplary embodiment of the method of the present invention is shown in the following Reaction Scheme 1.

[Reaction Scheme 1]

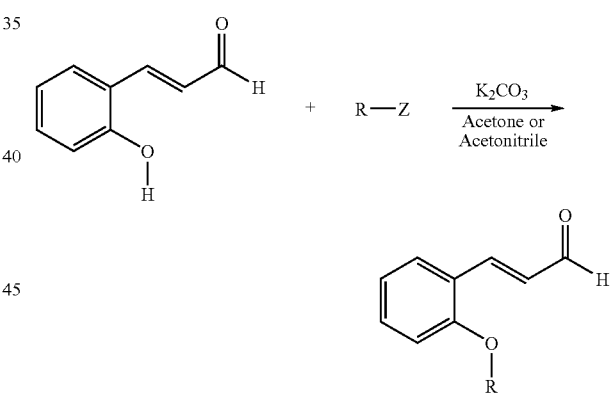

In Reaction Scheme 1, hydroxycinnamaldehyde is dissolved in an organic solvent and is then reacted with substituted acetyl chloride, substituted benzoyl chloride, picolyl chloride or piphenyl carbonyl chloride. The reaction is carried out in the presence of a carbonate compound for more than 10 hours, and preferably for 11 to 13 hours. As the organic solvent, for example, acetonitrile or acetone may be used.

In a further preferred aspect, the method further includes the step of 2) dissolving the compound obtained in the step 1) in an organic solvent, adding hydrochloric acid to the solution, and allowing the mixture to react. As the organic solvent, for example, acetonitrile or acetone may be used.

The additional step may further enhance the water solubility of the compound.

For structural characterization of the compound prepared according to the present invention, the purified compound is first analyzed for its molecular weight and molecular formula using ultraviolet (UV) and infrared (IR) absorbance spectroscopy and high-resolution mass spectrometry. In detail, UV spectroscopy is performed using a Shimadzu UV-265 spectrophotometer, and IR spectroscopy is performed using a Bio-Rad Digilab Division FTS-80 spectrophotometer. The molecular weight and molecular formula are determined by recording high-resolution mass spectra on a VG70-SEQ mass spectrometer. Also, $^1$H- and $^{13}$C-NMR spectra are obtained using a Varian 300 MHz or 500 MHz NMR spectrometer, and the NMR spectra are analyzed to determine the structure of the compound.

In a further aspect, the present invention provides an anticancer composition comprising a cinnamaldehyde compound represented by Chemical Formula 1 or a pharmaceutically acceptable salt thereof as an effective ingredient.

The term "anticancer", as used herein, is meant to include both the prevention and treatment of cancer.

Examples of cancer include colon cancer, lung cancer, non-small cell lung cancer, bone cancer, pancreatic cancer, skin cancer, head or neck cancer, cutaneous or ocular melanoma, uterine cancer, ovarian cancer, rectal cancer, gastric cancer, perianal cancer, breast cancer, fallopian tube carcinoma, endometrial carcinoma, uterine cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, uterine cancer, penis cancer, prostate cancer, chronic or acute leukemia, lymphocyte lymphoma, bladder cancer, kidney cancer, ureter cancer, renal cell carcinoma, renal pelvic carcinoma, and central nervous system (CNS) tumors.

The compound according to the present invention may be useful in the treatment and prevention of cancer because it is highly effective in inhibiting the abnormal growth of cancer cells.

In practice, when human colon carcinoma SW620 cells are dosed with 10 to 20 µM of the compound of Chemical Formula 1, the compound induces a cell cycle arrest in the G2/M phase, leading to cell growth inhibition. The inhibition of the growth of cancer cells may be tested as follows. In brief, human colon carcinoma SW620 cells were dosed with the compound dissolved in DMSO. After 48 hrs, nuclear DNA was stained with propidium iodide. The stained cells were analyzed to determine the cell cycle using a FACSCalibur cytometer (Becton-Dickinson, San Jose, Calif., USA). The proportions of cells in G1, S and G2/M phases were determined using a Becton-Dickinson Modifit cell-cycle analysis program and expressed as percentages.

The anticancer composition comprising the compound of Chemical Formula 1 according to the present invention may further include a suitable carrier, excipient or diluent according to an ordinary method. Examples of carriers, excipients and diluents include lactose, dextrose, sucrose, sorbitol, mannitol, xylitol, erythritol, maltitol, starch, arabic gum, alginate, gelatin, calcium phosphate, calcium silicate, cellulose, methyl cellulose, microcrystalline cellulose, polyvinyl pyrrolidine, water, methylhydroxybenzoate, propylhydroxybenzoate, talc, magnesium stearate, and mineral oil.

The present composition may be formulated for oral administration in the form of powders, granules, tablets, capsules, suspensions, emulsions, syrups or aerosols. It may be formulated in a form suitable for topical application, suppositories or sterile injectable solutions.

In detail, a formulation may be prepared with generally used diluents or excipients, such as fillers, thickeners, binders, humectants, disintegrators and surfactants. Solid formulations for oral administration may include tablets, pills, powders, granules and capsules, and are prepared by mixing the above compound with one or more excipients, such as starch, calcium carbonate, sucrose, lactose and gelatin. Also, the solid formulations may include, in addition to a simple excipient, a lubricant such as magnesium stearate or talc. Liquid formulations for oral administration may include suspensions, internal solutions, emulsions and syrups. The liquid formulations may include, in addition to commonly used simple diluents, such as water and liquid paraffin, various excipients, which are exemplified by humectants, sweeteners, aromatics and preservatives. Formulations for parenteral administration may include sterile aqueous solutions, non-aqueous solutions, suspensions, emulsions, lyophilized preparations, and suppositories. Non-aqueous solutions and suspensions may be prepared with propylene glycol, polyethylene glycol, vegetable oils such as olive oil, and injectable esters such as ethyl oleate. As a base for suppositories, Witepsol, macrogol, Tween 61, cacao oil, laurin oil and glycerinated gelatin may be used.

The preferred dosage of the present compound may vary depending on the patient's conditions and weight, the severity of illness, the type of formulation, administration route and the duration of treatment, but may be selected appropriately by a person skilled in the art. However, for desired effects, the present compound may be administered in a daily dosage of 1 to 50 mg/kg, and preferably 5 to 50 mg/kg. The daily dosage may be taken in a single dose, or may be divided into several doses.

In pharmaceutical dosage forms, the present compound may be used in the form of pharmaceutically acceptable salts thereof, and also may be used singly or in appropriate association, as well as in combination with other pharmaceutically active compounds.

The anticancer composition of the present invention may be administered to mammals, such as rats, mice, livestock and humans, via various routes. All modes of administration are contemplated, for example, administration can be made orally, rectally or by intravenous, intramuscular, subcutaneous, intrathecal, epidural or intracerebroventricular injection.

A better understanding of the present invention may be obtained through the following examples which are set forth to illustrate, but are not to be construed as the limit of the present invention.

EXAMPLE 1

Preparation of the Compound of Chemical Formula 2

1 g of hydroxycinnamaldehyde was dissolved in 200 ml of acetone. Then, 2 g of potassium carbonate and 0.8 g of methoxy acetyl chloride were added to the solution and mixed with stirring for 5 hrs at room temperature. After the reaction was completed, organic solvent phases containing an active substance were collected and concentrated under reduced pressure. 1.2 g of the concentrate was dissolved in 30 ml of methylene chloride and subjected to column chromatography, which was performed using a silica gel (Merck, Art No. 9385) with a mixture of ethylacetate and hexane (30:70). Active fractions were collected to obtain 1.3 g (yield: 90%) of a pale yellow compound (the compound of Chemical Formula 2). The physicochemical properties of the compound of Chemical Formula 2 are given in Table 1, below, and the proton NMR spectrum of the compound is shown in FIG. 1.

TABLE 1

| | |
|---|---|
| Appearance | Pale yellow |
| Molecular formula | $C_{12}H_{12}O_4$ |
| Molecular weight | 220.22 |
| Melting point | 47° C. |
| Solubility   Soluble | Alcohol, DMSO |
|   Insoluble | Hexane |
|   Water solubility | 320 µM |

$^1$H-NMR (CDCl$_3$): 9.69 (1H, d, J=7.2), 7.68 (1H, d, J=8.1), 7.51 (2H, m), 7.33 (1H, t, J=7.5), 7.22 (2H, d, J=8.1), 4.38 (2H, s), 3.56 (3H, s).

EXAMPLE 2

Preparation of the Compound of Chemical Formula 3

1 g of hydroxycinnamaldehyde was dissolved in 200 ml of acetone. Then, 2 g of potassium carbonate and 0.8 g of 4-picolyl chloride were added to the solution and mixed with stirring for 5 hrs at room temperature. After the reaction was completed, organic solvent phases containing an active substance were collected and concentrated under reduced pressure. 1.5 g of the concentrate was dissolved in 30 ml of methylene chloride and subjected to column chromatography, which was performed using silica gel (Merck, Art No. 9385) with a mixture of ethylacetate and hexane (60:40). Active fractions were collected to obtain 1.4 g (yield: 90%) of a pale yellow compound (the compound of Chemical Formula 3). The physicochemical properties of the compound of Chemical Formula 3 are given in Table 2, below.

TABLE 2

| | |
|---|---|
| Appearance | Pale yellow |
| Molecular formula | $C_{15}H_{13}O_2$ |
| Molecular weight | 239 |
| Melting point | 95° C. |
| Solubility   Soluble | Alcohol, DMSO |
|   Insoluble | Hexane, H$_2$O |

$^1$H-NMR (CDCl$_3$): 9.72 (1H, d, J=7.2), 8.65 (2H, m), 7.92 (1H, d, J=15.9), 7.61 (1H, m), 7.37 (3H, m), 7.05 (1H, t, J=7.2), 6.91 (1H, d, J=8.1), 6.81 (1H, m), 5.212 (2H, s).

EXAMPLE 3

Preparation of the Compound of Chemical Formula 4

Figure 2:
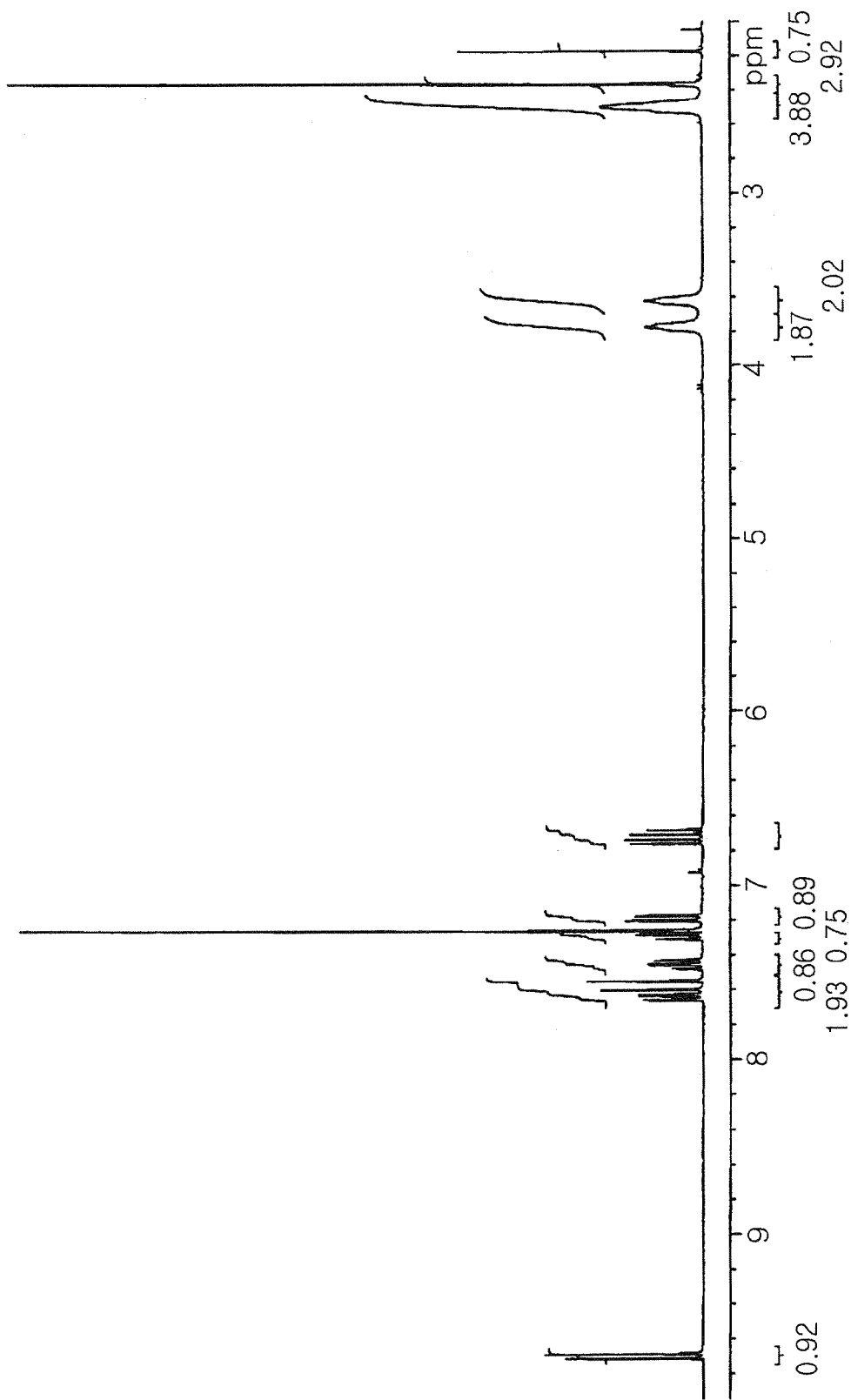
FIG. 2 is a proton NMR spectrum of a compound represented by Chemical Formula 4.

1 g of hydroxycinnamaldehyde was dissolved in 200 ml of acetone. Then, 2 g of potassium carbonate and 1.9 g of 4-methyl piperazine 1-carbonyl chloride were added to the solution and mixed with stirring for 5 hrs at room temperature. After the reaction was completed, organic solvent phases containing an active substance were collected and concentrated under reduced pressure. 1.5 g of the concentrate was dissolved in 30 ml of methylene chloride and subjected to column chromatography, which was performed using a silica gel (Merck, Art No. 9385) with a mixture of ethylacetate and methanol (99:1). Active fractions were collected to obtain 1.6 g (yield: 90%) of a pale yellow compound (the compound of Chemical Formula 4). The physicochemical properties of the compound of Chemical Formula 4 are given in Table 3, below, and the proton NMR spectrum of the compound is shown in FIG. 2.

TABLE 3

| | |
|---|---|
| Appearance | Pale yellow |
| Molecular formula | $C_{15}H_{18}N_2O_3$ |
| Molecular weight | 274 |
| Melting point | 100° C. |
| Solubility   Soluble | Alcohol, DMSO |
|   Insoluble | Hexane, H$_2$O |

$^1$H-NMR (CDCl$_3$): 9.69 (1H, d, J=7.2), 7.63 (2H, m), 7.45 (1H, m), 7.29 (1H, d, J=7.5), 7.18 (1H, m), 6.71 (1H, m), 3.77 (2H, m), 3.62 (2H, m), 2.49 (4H, m), 2.36 (3H, s).

EXAMPLE 4

Preparation of the Compound of Chemical Formula 5

1 g of hydroxycinnamaldehyde was dissolved in 200 ml of acetone. Then, 2 g of potassium carbonate and 1.2 g of benzenesulfonyl chloride were added to the solution and mixed with stirring for 5 hrs at room temperature. After the reaction was completed, organic solvent phases containing an active substance were collected and concentrated under reduced pressure. 1.9 g of the concentrate was dissolved in 30 ml of methylene chloride and subjected to column chromatography, which was performed using a silica gel (Merck, Art No. 9385) with a mixture of ethylacetate and hexane (30:70). Active fractions were collected to obtain 1.7 g (yield: 90%) of a pale yellow compound (the compound of Chemical Formula 5). The physicochemical properties of the compound of Chemical Formula 5 are given in Table 4, below.

TABLE 4

| | |
|---|---|
| Appearance | Pale yellow |
| Molecular formula | $C_{15}H_{12}O_4S$ |
| Molecular weight | 288 |
| Melting point | Liquid |
| Solubility   Soluble | Alcohol, DMSO |
|   Insoluble | Hexane |
|   Water solubility | 600 µM |

$^1$H-NMR (CDCl$_3$): 9.41 (1H, d, J=7.2), 7.81 (2H, m), 7.67 (1H, t, J=7.8), 7.49 (4H, m), 7.33 (1H, m), 7.27 (1H, m), 6.45 (1H, m).

EXAMPLE 5

Preparation of the Compound of Chemical Formula 6

1 g of the compound of Chemical Formula 3 was dissolved in 200 ml of acetone. Then, 1 ml of 37% hydrochloric acid was added to the solution and mixed with stirring for 10 hrs. After the reaction was completed, organic solvent phases containing an active substance were collected and concentrated under reduced pressure. The concentrate was recrystallized to obtain 1 g of the compound of Chemical Formula 6. The physicochemical properties of the compound of Chemical Formula 6 are given in Table 5, below.

TABLE 5

| | |
|---|---|
| Appearance | Pale yellow |
| Molecular formula | $C_{15}H_{14}ClNO_2$ |
| Molecular weight | 275 |
| Melting point | 187° C. |

| TABLE 5-continued | | |
|---|---|---|
| Solubility | Soluble | Alcohol, $H_2O$ |
| | Insoluble | Hexane, acetone |

$^1$H-NMR ($CDCl_3$): 9.74 (1H, d, J=7.2), 8.75 (2H, d, J=6), 7.91 (1H, d, J=16.2), 7.53 (2H, m), 7.63 (1H, m), 7.41 (1H, t, J=7.2), 7.11 (1H, t, J=7.2), 6.85 (2H, m), 5.37 (2H, s).

EXAMPLE 6

Preparation of the Compound of Chemical Formula 7

1 g of the compound of Chemical Formula 4 was dissolved in 200 ml of acetone. Then, 1 ml of 37% hydrochloric acid was added to the solution and mixed with stirring for 10 hrs. After the reaction was completed, organic solvent phases containing an active substance were collected and concentrated under reduced pressure. The concentrate was recrystallized to obtain 1 g of the compound of Chemical Formula 7. The physicochemical properties of the compound of Chemical Formula 7 are given in Table 6, below.

TABLE 6

| Appearance | Pale yellow |
|---|---|
| Molecular formula | $C_{15}H_{19}ClN_2O_3$ |
| Molecular weight | 310 |
| Melting point | 125° C. |
| Solubility   Soluble | Alcohol, $H_2O$ |
|              Insoluble | Hexane, acetone |

$^1$H-NMR ($CDCl_3$): 9.71 (1H, d, J=7.2), 7.62 (1H, m), 7.51 (2H, m), 7.33 (1H, t, J=6.6), 7.16 (1H, d, J=7.5), 6.68 (1H, m), 4.38 (2H, m), 4.13 (1H, m), 3.89 (1H, m), 2.88 (4H, s).

EXPERIMENTAL EXAMPLE 1

Cell Cycle Analysis

For flow cytometric analysis, human colon carcinoma SW620 cells were plated in T25 flasks (containing 7.5 ml of culture medium) and cultured in RPMI 1640 and DMEM media, each of which was supplemented with 10% FBS, in an incubator at 37° C. for 12 hrs. Then, as a control, DMSO was added to the culture medium at a final concentration of 0.1% (7.5 μl). As compound treatment groups, 7.5 μl of each of compounds dissolved in DMSO at various concentrations was added to the culture medium. After 48 hours, control (DMSO) and compound-treated cells were harvested and subjected to flow cytometric analysis.

After the culture media were removed from flasks, cells were trypsinized and centrifuged at 300 g for 5 min. The collected cells were washed with phosphate buffer twice to remove culture media. The cells were then fixed in 3 ml of 70% ethanol at −20° C. for 12 hrs. The fixed cells were centrifuged at 300 g for 5 min and washed with cold PBS twice to remove remaining ethanol. The washed cells were resuspended in 500 μl of PBS, and treated with 50 μl of 100 μg/ml RNase A at 37° C. for 30 min. Then, cells were incubated in 10 μl of 1 mg/ml propidium iodide (PI) in PBS for DNA staining. The cell cycles of 20,000 stained cells were analyzed using a FACSCalibur cytometer (Becton-Dickinson, San Jose, Calif., USA). Cell cycle fractions were quantified using a Becton-Dickinson Modifit cell-cycle analysis program, and the distribution of cells in G1, S and G2/M phases was expressed as percentages.

The results of this test to evaluate the effects of the compounds of Chemical Formulas 2 to 7 on cell cycle are given in Tables 7 to 13, below.

TABLE 7

Cell cycle inhibitory activity of the compound of Formula 2 in cancer cells

| Cancer | | | Cell distribution (%) | | |
|---|---|---|---|---|---|
| cell line | Compound | Conc. | G0-G1 | S | G2-M |
| SW620 | Control | 20 μM | 56.15 | 30.32 | 13.53 |
| | Compound of Formula 2 | | 33.00 | 17.06 | 49.94 |

TABLE 8

Cell cycle inhibitory activity of the compound of Formula 3 in cancer cells

| Cancer | | | Cell distribution (%) | | |
|---|---|---|---|---|---|
| cell line | Compound | Conc. | G0-G1 | S | G2-M |
| SW620 | Control | 20 μM | 58.83 | 21.23 | 19.94 |
| | Compound of Formula 3 | | 39.80 | 26.57 | 33.63 |

TABLE 9

Cell cycle inhibitory activity of the compound of Formula 4 in cancer cells

| Cancer | | | Cell distribution (%) | | |
|---|---|---|---|---|---|
| cell line | Compound | Conc. | G0-G1 | S | G2-M |
| SW620 | Control | 30 μM | 60.12 | 28.35 | 11.54 |
| | Compound of Formula 4 | | 37.50 | 17.01 | 45.49 |

TABLE 10

Cell cycle inhibitory activity of the compound of Formula 5 in cancer cells

| Cancer | | | Cell distribution (%) | | |
|---|---|---|---|---|---|
| cell line | Compound | Conc. | G0-G1 | S | G2-M |
| SW620 | Control | 20 μM | 75.15 | 22.52 | 2.33 |
| | Compound of Formula 5 | | 36.01 | 18.05 | 45.94 |

TABLE 11

Cell cycle inhibitory activity of the compound of Formula 6 in cancer cells

| Cancer | | | Cell distribution (%) | | |
|---|---|---|---|---|---|
| cell line | Compound | Conc. | G0-G1 | S | G2-M |
| SW620 | Control | 40 μM | 55.12 | 19.18 | 25.70 |
| | Compound of Formula 6 | | 43.85 | 14.84 | 41.31 |

TABLE 12

Cell cycle inhibitory activity of the compound of Formula 6 in cancer cells

| Cancer cell line | Compound | Conc. | Cell distribution (%) | | |
|---|---|---|---|---|---|
| | | | G0-G1 | S | G2-M |
| SW620 | Control | 20 μM | 60.83 | 19.23 | 19.94 |
| | Compound of Formula 6 | | 39.80 | 26.57 | 33.63 |

TABLE 13

Cell cycle inhibitory activity of the compound of Formula 7 in cancer cells

| Cancer cell line | Compound | Conc. | Cell distribution (%) | | |
|---|---|---|---|---|---|
| | | | G0-G1 | S | G2-M |
| SW620 | Control | 30 μM | 58.15 | 30.33 | 11.52 |
| | Compound of Formula 7 | | 35.11 | 17.06 | 47.83 |

As shown in Tables 7 to 13, the compounds of Chemical Formulas 2 to 7 were found to arrest the cell cycle of cancer cells in the G2/M phase, and thus to block cell division. These results indicated that the compounds of the present invention inhibit the abnormal growth of cancer cells and thus have the potential to treat or prevent cancer.

EXPERIMENTAL EXAMPLE 2

Evaluation of Anticancer Activity of the Present Compound Upon Oral Administration to Tumor-Xenografted Nude Mice Nude mice were divided into three groups: a compound administration group, a vehicle control group and a positive control group. A 0.3-ml aliquot of human colon carcinoma HT-29 cells ($3 \times 10^7$ cells/ml) was injected subcutaneously into the right axilla between the scapular region and the chest wall of mice. From the day (Day 1) after tumor transplantation to the day before sacrifice, the compound of Chemical Formula 6 was administered orally at a dose of 10 mg/kg once every day. As a positive control, adriamycin (ADM) was administered at a dose of 2 mg/kg, and the other test conditions were the same as in the compound treatment group.

In order to investigate the clinical signs of drug toxicity, animals were monitored for change in body weight about three times a week during the test period. From Day 6 to Day 18 after tumor transplantation, tumor size was measured five times for the mice of each group.

Tumor diameter was measured in three planes with a vernier caliper. Tumor volume (V) was calculated using the following Equation 1.

Tumor volume=(Length×Width×Height)/2    [Equation 1]

On Day 18 of tumor transplantation, animals were sacrificed, and tumors were excised and weighed.

Body weight change was investigated in nude mice implanted with HT-19 carcinoma for the test period of 18 days after drug administration. Compared to vehicle control mice, no weight changes were observed in compound-received mice. In contrast, the positive control group (dosed with adriamycin (ADM)) exhibited a statistically significant weight loss of 10.3% (p<0.001).

Figure 3:
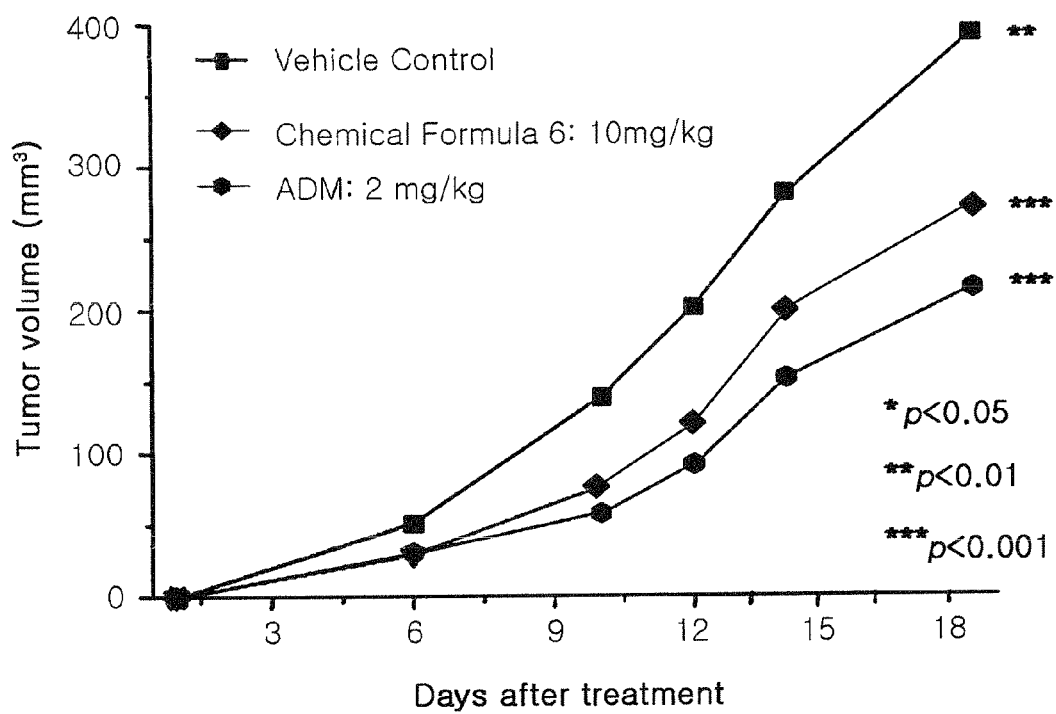
FIG. 3 is a graph showing the inhibitory effects of a compound represented by Chemical Formula 6 on tumor growth in nude mice implanted with HT-29 carcinoma.

As shown in FIG. 3, the compound of Chemical Formula 6 was found to have statistically significant tumor growth inhibitory effect of 30.7% (p<0.001). The positive control group displayed statistically significant tumor growth inhibition of 45.4% (p<0.001).

EXPERIMENTAL EXAMPLE 3

Evaluation of Acute Toxicity of the Present Compound Upon Oral Administration to Rats An acute toxicity test was performed in order to evaluate the toxicity of the cinnamaldehyde derivatives according to the present invention.

The acute toxicity test was carried out using 6-week-old specific pathogen-free (SPF) SD rats, as follows. The cinnamaldehyde derivatives prepared in Examples were dissolved in injectable distilled water and administered orally to groups each consisting of two rats at a single dose of 1000 mg/kg. After the test compounds were administered, death, clinical symptoms and body weight change were observed, and a hematological test and hematobiochemical analysis were performed. Upon autopsy, abnormalities in abdominal organs and chest organs were visually observed.

As a result, none of the rats that received the test compounds exhibited any particular clinical symptoms, death, change in weight, or toxicity upon the hematological assay, hematobiochemical analysis and autopsy.

Taken together, the cinnamaldehyde derivatives according to the present invention exhibited no toxicity even at a dose of 1000 mg/kg in all rats, and had a 50% lethal dose ($LD_{50}$) upon oral administration in amounts greater than 1000 mg/kg. These results indicated that the present compounds are safe.

As described hereinbefore, the cinnamaldehyde compound of Chemical Formula 1 or pharmaceutically acceptable salts thereof according to the present invention induce a G2/M cell cycle arrest in cancer cells, thereby inhibiting the abnormal growth of the cells, and also have improved solubility in water, thereby exhibiting higher anticancer effects. Thus, a composition comprising the compound according to the present invention is useful in preventing and treating cancer diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cinnamaldehyde compound represented by Chemical Formula 1, below, or a pharmaceutically acceptable salt thereof:

[Chemical Formula 1]

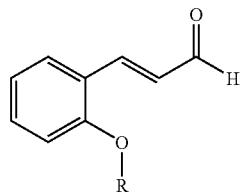

wherein, R is a ($C_4$-$C_{10}$) heteroaryl having one nitrogen heteroatom.

2. The cinnamaldehyde compound or pharmaceutically acceptable salt thereof as set forth in claim 1, wherein the R is picolyl.

3. The cinnamaldehyde compound or pharmaceutically acceptable salt thereof as set forth in claim 1, which is selected from the group consisting of

[Chemical Formula 3]

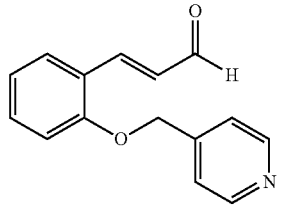

and

[Chemical Formula 6]

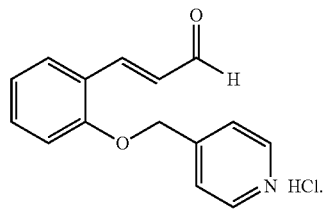

4. A method of preparing a cinnamaldehyde compound represented by Chemical Formula 1, below, comprising the step of 1) reacting hydroxycinnamaldehyde, represented by Chemical Formula 8, below, with a compound represented by Chemical Formula 9 to yield the compound of Chemical Formula 1:

[Chemical Formula 1]

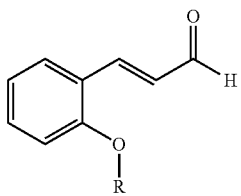

[Chemical Formula 8]

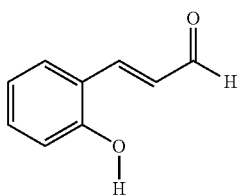

R—Z                                 [Chemical Formula 9]

wherein, R is a ($C_4$-$C_{10}$) heteroaryl having one nitrogen heteroatom; and

Z is a leaving group.

5. The method as set forth in claim 4, wherein the R is picolyl; and Z is chlorine (Cl) or Bromine (Br).

6. The method as set forth in claim 4, further comprising the step of 2) dissolving the compound obtained in the step 1) in an organic solvent, adding hydrochloric acid to a resulting solution, and allowing a resulting mixture to react.

7. The method as set forth in claim 6, wherein the organic solvent is acetonitrile or acetone.

8. An pharmaceutical composition for treating colon cancer, comprising the compound according to any one of claims 1 to 3 as an effective ingredient.

9. A method of treating colon cancer, comprising administering the compound according to claim 1.

* * * * *